United States Patent [19]
Marliere et al.

[11] Patent Number: 5,407,797
[45] Date of Patent: Apr. 18, 1995

[54] OLIGONUCLEOTIDE PROBES AND METHODS FOR DETECTING BY HYBRIDIZATION THE NUCLEIC ACIDS OF BACTERIA AND OTHER LIVING ORGANISMS

[75] Inventors: Philippe Marliere; Patrick Grimont, both of Paris, France

[73] Assignees: Institut Pasteur; Institut National de la Sante et de la Recherche Medicale, both of Paris, France

[21] Appl. No.: 3,875

[22] Filed: Jan. 11, 1993

Related U.S. Application Data

[63] Continuation of Ser. No. 711,411, Jun. 5, 1991, abandoned, which is a continuation of Ser. No. 596,553, Oct. 12, 1990, abandoned, which is a continuation of Ser. No. 97,519, Sep. 28, 1987, abandoned.

[30] Foreign Application Priority Data

Apr. 4, 1986 [FR] France ................. 86 04914

[51] Int. Cl.$^6$ ............. C12Q 1/68; C07H 21/00; C07H 21/04
[52] U.S. Cl. ........................ 435/6; 536/23.1; 536/24.3; 536/24.31; 536/24.32; 536/24.33; 935/77; 935/78
[58] Field of Search ............ 435/6, 91; 436/501; 536/23.1, 24.1, 24.31–24.33; 935/78

[56] References Cited

FOREIGN PATENT DOCUMENTS

| 0155359 | 7/1985 | European Pat. Off. . |
| 0174226 | 2/1986 | European Pat. Off. . |
| 84/03716 | 4/1984 | WIPO . |
| 8402721 | 7/1984 | WIPO . |

OTHER PUBLICATIONS

Van Duin et al. (1984) Nucleic Acids Research, vol. 12, No. 12, pp. 5079–5086.
Gray et al. (1984) Nucleic Acids Research, vol. 12, No. 14, pp. 5837–5852.
Woese et al. (1983) Microbiology Reviews, vol. 47, No. 4, pp. 621–669.
Mankin et al. (1985) Gene, vol. 37, pp. 181–189.
Lane et al, *Proc. Natl. Acad. Sci. USA*, vol. 82, pp. 6955–6959 (Oct. 1985).
Frydenberg et al, *Chemical Abstracts*, vol. 103, No. 5, p. 95, 32819k (Aug. 5, 1985).

*Primary Examiner*—Margaret Parr
*Assistant Examiner*—Ardin H. Marschel
*Attorney, Agent, or Firm*—Oblon, Spivak, McClelland, Maier, & Neustadt

[57] ABSTRACT

The invention relates to a hybridization probe for detecting the existence of bacteria in a sample. It consists of one of the two pentadecadeoxyribonucleotides of sequence (5')d - AAG GAG GTG ATC CAG (3'), (5')d - CTG GAT CAC CTC CTT (3').

12 Claims, No Drawings

OLIGONUCLEOTIDE PROBES AND METHODS FOR DETECTING BY HYBRIDIZATION THE NUCLEIC ACIDS OF BACTERIA AND OTHER LIVING ORGANISMS

This application is a continuation of application Ser. No. 07/711,411, filed on Jun. 5, 1991, now abandoned, which is a continuation of Ser. No. 07/596,553, filed on Oct. 12, 1990, now abandoned, which is a continuation of Ser. No. 07/097,519, filed on Sep. 28, 1987, now abandoned.

Doctors, veterinarians, plant pathologists and biologists generally often have to determine whether a sample (human, animal, vegetable, foodstuff or other) contains bacteria or possibly other organisms. At present, the only means which can be used for detecting the presence of living microorganisms are microscopy (light or electron), culturing, immunological detection and detection by specific nucleic acid probes.

Immunological detection and detection by specific nucleic acid probes are currently applied only to particular organisms, for example *Legionella pneumophila* or *Salmonella*. A reagent which enables one or more organisms to be detected is generally incapable of detecting the other species or genera (this principle of specificity is the grounds for using these reagents).

Microscopic examination is necessarily limited to a small portion of the sample, and cell debris or other particles can make it impossible to visualize a living organism and identify it as such.

Culturing is possible for only a certain number of organisms (in particular, bacterial) and on certain media and under conditions specific to these organisms (aerobic or anaerobic bacteria, requiring some particular growth factor, or the like). No culture medium can, on its own, permit the growth of all bacteria capable of being cultured. It is possible for bacteria to be unknown and undetectable at the present time because it is not known how to culture them. There are abundant examples of cases where the presence of bacteria could be proved only after one or more years of research: in Legionnaire's disease (Philadelphia epidemic), the bacteria responsible, which the human samples were subsequently shown to contain, were not visible after the usual staining in the microscope and could not be cultured on the bacteriological media known at the time. Similarly, bacteria which infect the xylem of plants were unknown for a long time. They were only discovered as the result of painstaking observations under the microscope. As in the above case, these bacteria could not be cultured on the media known at the time. It follows from the above examples that the lack of detection of a bacterial contamination in a medium being studied by the means traditionally used cannot necessarily lead to the conclusion that this medium is devoid of all bacterial contamination.

The objective of the invention is to remedy the deficiencies of the traditional detection techniques, in other words to provide a method which enables either the sterile nature of a particular medium, for example a human sample, to be confirmed, or the existence of a contamination, for example a bacterial contamination, to be revealed with a degree of reliability hitherto unknown.

It will be readily appreciated that such a method can be extremely useful, since it would enable contamination of a sample with bacteria or other cells to be detected, there even being a possibility of counting the cells. A detection of this kind could not fail, for example, to stimulate effectively the search for a bacterium in cases of infection (human, animal, plant) of unknown aetiology.

The invention derives from the interest, on the part of the inventors, in the study of ribosomal RNAs. Of all the macromolecular constituents of living organisms, the ribosomal ribonucleic acids (RNA) appear a priori to be reliable indicators of a biological contamination (presence of living organisms). These RNAs form a substantial part of the cellular material. They are necessary for the functioning of all known living cells.

The RNA of the small ribosomal subunit (known as 16S RNA by reference to its sedimentation constant in ultracentrifugation with a sucrose gradient) is now known at the nucleotide level for some 20 organisms (examples of complete nucleotide sequences are given by Weisburg et al. 1985, *J. Bacteriol.* vol. 164, No. 1, p. 230-236; Frydenberg and Christiansen, 1985, DNA vol. 4, No. 2, p. 127-137). The nucleotides are conventionally numbered from the 5' end of the 16S RNA molecule to the 3' end. The 16S RNA of the *Escherichia coli* bacterium comprises 1542 nucleotides. The corresponding molecules in the other living organisms can differ from that of *E. coli* in their total number of nucleotides and in their nucleotide sequence.

The comparison of the nucleotide sequences of the known ribosomal RNAs and the discovery of portions which are common to them with a degree of identity, in all cases of extreme resemblance extending beyond the levels of sequence conservation which could be expected, were the factors which led to the invention. Thus, it has been found that the variations between different organisms are not distributed throughout the 16S RNA sequences, but are concentrated in certain places (in particular in the coils of the structure), while certain regions (the loops in particular) appear to be much more highly conserved. Moreover, these variations agree in a consistent manner with the large taxonomic divisions. Thus, in the 16S RNA sequences, it is possible to define universal units, specifically eucaryotic and bacterial (procaryotic) units and units specific to more restricted bacterial groups.

The 16S RNAs were thus shown to possess a universal region (that is to say, common to eucaryotes and procaryotes) extending from nucleotide 1492 to nucleotide 1506 (following the numbering in use for the 16S RNA sequence of *E. coli*) and a region specific to bacteria (eubacteria, archaebacteria, and methanogenic and halophilic bacteria) extending from nucleotide 1527 to nucleotide 1541. In this connection, reference may be made to the table on the following page, in which A, T, C and G denote the 4 standard nucleotides which participate in the composition of DNAs; it is understood that the nucleotide designated by a given reference number corresponds to that placed under the first figure of the number. For example, the number 1490 corresponds to uraciL (U) in the nucleotide sequence corresponding to the RNA.

The transfer RNAs of a large number of bacteria were also shown to contain common sequences, in particular

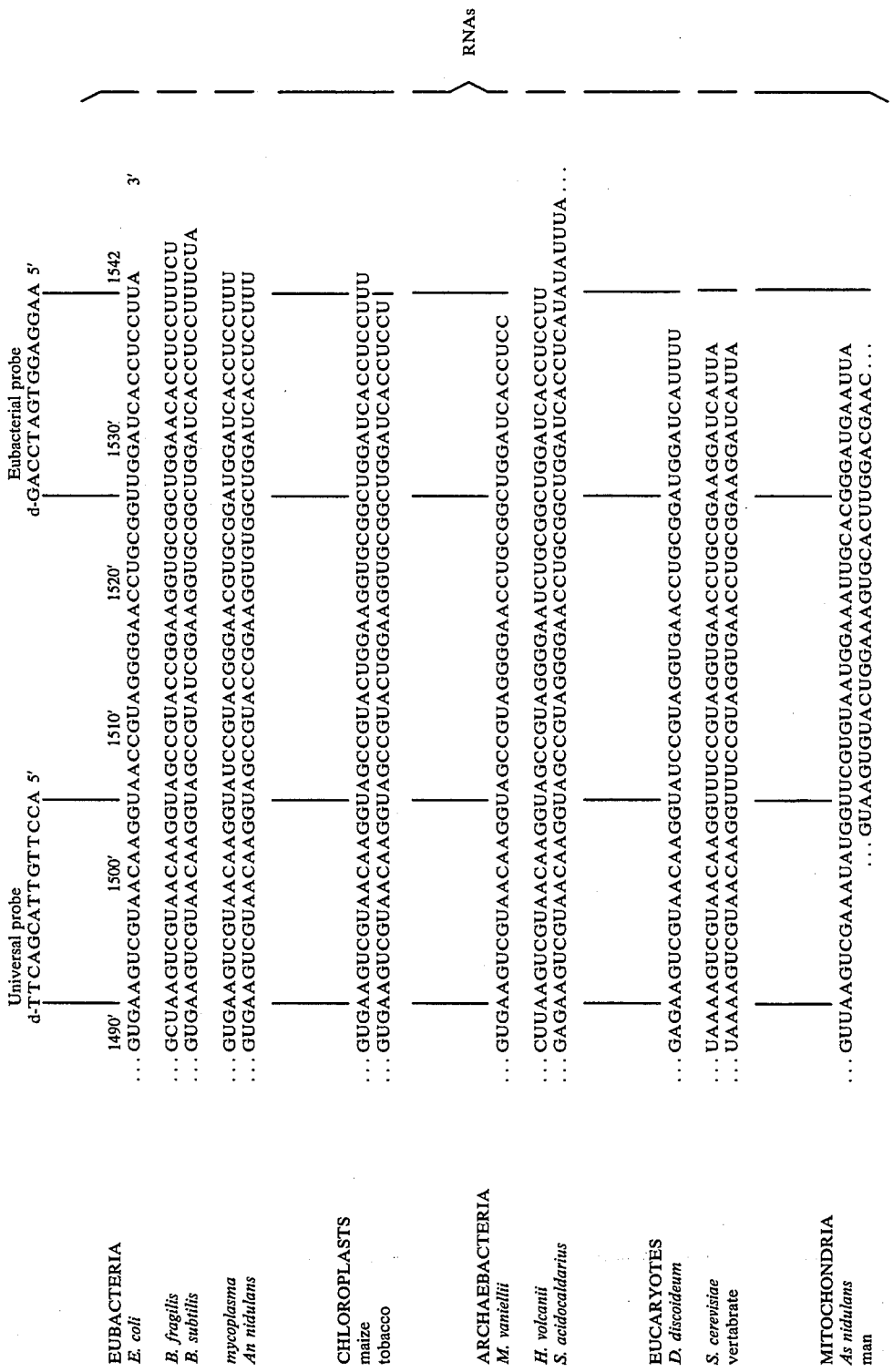

the following:

UCAUAACCCGAAGGUC.

This sequence appears, however, to be less universal than the region specific to bacteria mentioned above, which extends from nucleotide 1527 to nucleotide 1541.

The archaebacteria were also shown to possess a sequence common to all this bacterial type, which sequence possesses the following structure:

UUCGACGAGRUGGGGCGC in which R is A or G.

The invention hence derives from the above findings, and it provides specific nucleotide sequences which are complementary to the above sequences and which constitute a similar number of probes, some of which are applicable universally to the detection of a cellular contamination in any medium, others being applicable to the classification of the cells possibly detected among the following categories:

as bacteria, including certain archaebacteria, more especially methanogenic and halophilic archaebacteria, as archaebacteria, and into all other categories of organisms, in the case of positive response in hybridization tests with the "universal probe" and negative response with the probes which permit the classification of the microorganisms detected into the categories designated above.

The sequences of the type in question are readily accessible by nucleotide synthesis. The invention hence relates more especially to a pentadecadeoxyribonucleotide deoxyribonucleic acid sequence of 15 nucleotides, or 15-mer for short) which is complementary to the 1492-1506 region of the 16S RNAs, this 15-mer being capable of hybridizing with the homologous fragment present in the 16S RNA of all living organisms as well as with the portion of the deoxyribonucleic acid (DNA) which codes for this RNA portion and which is present in the genome of all living organisms.

It also relates to the probes which consist of the oligonucleotides which are complementary to the sequence UCAUAACCCGAAGGUC already mentioned, for the detection of microorganisms capable of being classified among bacteria, and the probes which are complementary to the abovementioned sequence UUCGACGAGRUGGGGCGC, these probes themselves being characteristic of archaebacteria.

The invention finally relates to a DNA sequence of 15 nucleotides (15-mer) which is complementary to the 1527-1541 region of the 16S RNAs, this 15-mer being capable of hybridizing with the homologous fragment present in the 16S RNA of bacteria and other procaryotes, as well as with the corresponding genes in the DNA of these organisms, but incapable or only very slightly capable of hybridizing with the corresponding RNA of eucaryotic cells (yeasts, fungi, protozoa, human, animal and plant tissues) or the corresponding genes in the DNA of these organisms.

The invention consequently relates more especially to the following compositions:

Probe hereinafter referred to as "Universal probe"

The probe produced by oligonucleotide synthesis has the following sequence:

(5')d - ACC TTG TTA CGA CTT (3')

where (5') and (3') indicate the 5' and 3' ends of the polymer (and hence its polarity) and where the letters indicate the following deoxynucleotides: A, adenyl residue; C, cytidyl residue; T, thymidyl residue; and G, guanidyl residue; the spaces serving only in the interest of legibility of the sequence which contains 15 nucleotides.

This probe is fully complementary to the 1492-1506 portion (according to the number in use for *Escherichia coli*) of the 16S RNA of this microorganism, and to corresponding portions of the published RNAs of all other bacteria, procaryotic and eucaryotic cells and, albeit to a lesser extent, with RNAs of mitochondria. The expert will deduce from this that there is the virtually total probability that this probe must also appear with the RNAs of all cells existing in nature. This probe is also capable of pairing with the homologous portion of the DNA of the genes which code for these 16S RNAs and corresponding eucaryotic RNAs.

The invention naturally also relates to the probe which is complementary to the abovementioned "universal probe" and has the following nucleotide sequence:

(5')d - AAG TCG TAA CAA GGT (3')

which is capable of pairing with the same portion of genomic DNA (genes coding for the 16S RNAs and corresponding RNAs) on account of its double-stranded nature, even though it is no longer capable of pairing with the 16S RNA (which contains only a single strand).

Probe hereinafter referred to as "Composition specific for eubacteria and certain archaebacteria" or "eubacterial probe"

The preferred probe produced by oligonucleotide synthesis has the following sequence:

(5')d - AAG GAG GTG ATC CAG (3')

where (5'), (3'), A, C, T and G have the meanings stated above.

This sequence corresponds to the complement of the concensus sequence of the 1527-1541 portion (according to the number in use for *Escherichia coli*) of the 16S RNAs of bacteria and, more precisely, of eubacteria. This sequence is not fully complementary to all the 16S RNA sequences published to date for bacteria, but it differs therefrom at most by only one or two nucleotides. In contrast, the sequence of this composition can pair only weakly with the homologous region of the 18S RNAs of eucaryotes and 12S RNAs of mitochondria (these RNAs correspond to the 16S RNAs of bacteria).

The invention naturally also relates to any probe capable of pairing with the same regions of the RNAs and/or genomic DNA, especially a sequence shifted by one nucleotide with respect to the "eubacterial probe" described above, in that it pairs with the sequence UGGAUCACCUCCUUA, the probe then consisting of the sequence:

(3') ACCTAGTGGAGGAAA (5') or (if the reading direction is reversed)

(5')d - AAAGGAGGTGATCCA (3')

which occurs in the majority of bacteria.

It naturally also relates to any smaller oligonucleotide probe whose sequence is nevertheless contained in the abovementioned "specific probe for eubacteria" (or in the probe containing the "shifted sequence").

This probe nevertheless contains at least the sequence TGGAGGAA (5') (which is complementary to the region of the 16S RNA extending between nucleotides 1534 and 1541), in particular (5')d - AAGGAGGT (3')

(5')d - AAAGGAGGT (3')

(5')d - AAGGAGGTG (3')

(5')d - AAGGAGGTGA (3')
(5')d - AAGGAGGTGAT (3')
(5')d - AAGGAGGTGATC (3')
(5')d - AAGGAGGTGATCC (3')
(5')d - AAGGAGGTGATCCA (3').

The sequences complementary to the above also form part of the group of probes according to the invention.

It is nevertheless appropriate to stress the fact that the longest probes are preferred on account of their greater pairing stability. Moreover, the substitution of one nucleotide by another within the same sequence would possibly endow them with higher affinity for the 16S RNAs of one specified bacterial group, but would weaken their complementarity with respect to the majority of the others. On the other hand, elongation performed at the 3' end with all or part of the unit CCGCA would not confer a gain in specificity, since the complement of its unit is represented in the 18S RNA of vertebrates.

Specific probe for archaebacteria

The invention finally relates more especially to a specific probe for archaebacteria, this probe possessing a sequence of at least 8 nucleotides contained in the following sequence:

AAGCTGCTCR'ACCCCGCG and at most the 18 nucleotides of the sequence, in which R' is T or C.

GENERAL CONDITIONS FOR USE OF THE PROBES

The universal probes and the more specific probes for eubacteria on the one hand, and archaebacteria on the other hand (and the complementary compositions) are advantageously labelled. Any traditionally envisaged label can be used. The compositions can be labelled using radioactive tracers such as $^{32}P$, $^{35}S$, $^{125}I$, $^{3}H$ or $^{14}C$, to mention only the most commonly used tracers. The radioactive labelling can be carried out according to any method such as, for example, terminal labelling at the 3' or 5' end using a radiolabelled nucleotide, polynucleotide kinase (with or without dephosphorylation with a phosphatase) or a ligase (depending on the end to be labelled). In these cases, the labelled composition would have 16 nucleotides (the radioactive nucleotide added at the 3' or 5' end being of any type). One of the probes of the invention (including a complementary composition) can serve as a template for the synthesis of a short strand (of approximately 15 nucleotides), consisting of radioactive nucleotides or an assembly of radioactive and non-radioactive nucleotides. The probes of the invention can also be produced by chemical synthesis using one or more radioactive nucleotides. Another method of radioactive labelling is the chemical iodination of the probes of the invention, leading to the binding of several $^{125}I$ atoms to the oligomers. If one of the probes of the invention (or a complementary probe) is made radioactive for use in hybridization with a non-radioactive RNA or DNA, the method of detecting the hybridization will depend on the radioactive tracer used, and may be based on autoradiography, liquid scintillation, gamma counting or any other technique which enables the ionizing radiation emitted by the radioactive tracer to be detected.

A non-radioactive labelling can also be used, combining the probes of the invention with residues having immunological properties (antigens, haptens), a specific affinity for certain reagents (ligands), properties enabling detectable enzyme reactions to be completed (enzymes or coenzymes, enzyme substrate, or other substance involved in an enzymatic reaction), or characteristic physical properties, such as fluorescence or the emission or absorption of light at any wavelength, to mention only some examples. Antibodies which specifically recognize DNA/RNA hybrids can also be used.

The chemical labelling which has just been mentioned can be carried out during the chemical synthesis of the probes of the invention, it being possible to couple the adenosine, guanosine, cytidine and thymidine residues to other chemical residues enabling the composition or the hybrids formed between the composition and a complementary DNA or RNA fragment to be detected. However, the sequence of the composition using nucleotides modified by coupling to other chemical residues would be the same as the nucleotide sequence of one of the probes of the invention.

The invention also relates to the methods for detection by hybridization, which themselves employ probes according to the invention, these probes having previously been labelled or made capable of being detected as stated above.

The choice of one or other of the probes of the invention will depend on the objective sought: detection of procaryotic and eucaryotic cells (universal composition), detection or localization of DNA or DNA fragments carrying genes which code for the RNAs of the 16S series and originating without discrimination from procaryotic or eucaryotic cells (universal composition or probe which is complementary thereto), exclusive detection of bacterial cells (specific probe for eubacteria), detection or localization of DNA or DNA fragments carrying the genes which code for the bacterial 16S RNAs (specific probe for eubacteria or probe which is complementary thereto). The use of one or more probes of the invention cannot be limited to a particular hybridization technique.

If cells originating from (or which are themselves living organisms) are to be detected, the RNAs and/or the DNA of these cells must be made accessible (by partial or total lysis of the cells using chemical or physical methods) and brought into contact with one or more of the probes of the invention, the probe(s) itself/themselves being made detectable. This contact can take place on a suitable support such as a nitrocellulose, cellulose (modified or unmodified) or nylon filter (to mention only the usual supports) or on a histological section or a cell smear or, without a support, in liquid medium. This contact takes place under optimal or restrictive conditions, that is to say conditions which permit the formation of hybrids only if the sequences are completely homologous over a length of molecule which increases in size as the conditions become more "restrictive") of temperature and ionic concentration, with or without substances which lower the optimal temperature for pairing of nucleic acids (formamide, dimethyl sulphoxide, urea), and with or without substances which apparently reduce the reaction volume (dextran, dextran sulphate).

The removal of unreacted molecules or fragments of molecules of the probe on a support can be carried out by washing with a buffer solution of suitable ionic strength and at a suitable temperature, with or without treatment with S1 nuclease or another enzyme which digests single-stranded DNA or single-stranded RNA but does not digest DNA/RNA hybrids or double-stranded DNA. In liquid medium, the molecules (or fragments) of the probe which have paired with RNA or DNA fragments can be separated from those which have not reacted by chromatography on hydroxyapatite or, after treatment with S1 nuclease, by all methods for separating double-stranded fragments from free nucleotides (chromatography on hydroxyapatite or on DEAE-cellulose, or exclusion chromatography; selective precipitation; dialysis; to mention only the most common methods).

The molecules (or fragments) of the composition used are then detected by the most advantageous method, depending on the type of labelling chosen.

The technical details described in various publications (Maniatis et al. 1982, *"Molecular cloning, A laboratory manual"*, Cold Spring Harbor Laboratory; Grimont et al. 1985, *J. Clin. Microbiol.* vol. 21, No. 3, pp. 431–437) or patents (French: 84/12,250, 78/10,975, 81/24,631; European: 0,133,288, 0,063,879) may advantageously be applied with the compositions of the invention.

If chromosomal DNA fragments carrying the genes which code for the 16S RNAs (or corresponding RNAs) are to be localized after treatment of the DNA with one or more restriction enzymes, separation of the fragments by electrophoresis or chromatography, and denaturation of the DNA fragments, that is to say separation of the two strands one of the probes of the invention is brought into contact with the DNA fragments under conditions which favour hybridization and, after the time required for completion of the hybridization, the unhybridized fragments of the composition will be separated from the hybridized fragments and the labelling visualized as stated for the detection of cells.

The technical details described in European Patent 0,120,658 (John A Webster Jr.) or in the work of Maniatis et al. or in the publication of Grimont et al. (cited above) can be applied with any of the probes of the invention. It should be noted that, for the localization of chromosomal DNA fragments carrying the genes which code for the 16S RNAs, one of the probes of the invention and a probe exactly complementary to it would give exactly the same results.

In general, the different probes of the invention can also be contained in recombinant DNAs which enable them to be cloned, inasmuch as the presence of a heterologous DNA would not impair the specificity of the probes in the applications envisaged.

Finally, it is understood that the probes in which the thymidine groups are replaced by uracil groups (the se probes hence having to be regarded as strictly equivalent to the probes which are more especially claimed) also form part of the invention, even though their synthesis is more difficult to accomplish.

We claim:

1. An oligonucleotide probe which is a DNA molecule having a sequence or a sequence fully complementary thereto and of equal length; said DNA molecule selected from group consisting of:
    (5') AAGGAGGT (3'),
    (5') AAAGGAGGT (3')
    (5') AAGGAGGTG (3')
    (5') AAGGAGGTGA (3')
    (5') AAGGAGGTGAT (3')
    (5') AAGGAGGTGATC (3')
    (5') AAGGAGGTGATCC (3')
    (5') AAGGAGGTGATCCA (3'),
    (5') AAGGAGGTGATCCAG (3'), and
    (5') AAAGGAGGTGATCCA (3'), wherein (5') and (3') indicate respectively the 5' and 3'ends of said sequence and A is an adenyl residue, C is a cytidyl residue, T is a thymidyl residue and G is a guanidyl residue, and
    wherein said probe is able to hybridize with the 16S RNA of procaryotes but which is incapable or only very slightly capable of hybridizing with the 18S RNAs of eucaryotes or the 12S RNAs of mitochondria.

2. The oligonucleotide probe according to claim 1, which is selected from the group consisting of:
    (5') AAG GAG GTG ATC CAG (3')
    (5') AAG GAG GTG ATC CA (3') and
    (5') A AAG GAG GTG ATC CA (3').

3. The oligonucleotide probe according to claim 1, wherein said probe is labelled with a radioactive label, said label selected from the group consisting of $^{32}P$, $^{35}S$, $^{125}I$, $^{3}H$ and $^{14}C$.

4. The oligonucleotide probe according to claim 1, wherein said probe is labelled with a nonradioactive label.

5. An oligonucleotide probe which is a DNA sequence having a sequence of
    (5') ACC TTG TTA CGA CTT (3'), or
    (5') AAG TCG TAA CAA GGT (3');

wherein (5') and (3') indicate respectively the 5' and 3' ends of said sequence and A is an adenyl residue, C is a cytidyl residue, T is a thymidyl residue and G is a guanidyl residue,
    wherein said probe is able to hybridize to the 16S RNA of procaryotes, the 18S RNAs of eucaryotes and the 12S RNAs of mitochondria.

6. The oligonucleotide probe according to claim 5, wherein said probe is labelled with a radioactive label, said label selected from the group consisting of $^{32}P$, $^{35}S$, $^{125}I$, $^{3}H$ and $^{14}C$.

7. The oligonucleotide probe according to claim 5, wherein said probe is labelled with a nonradioactive label.

8. An oligonucleotide probe which is a DNA molecule having a sequence:
    (5') GCG CCC CAR' CTC GTC GAA (3'),
or a fragment thereof which comprises at least 8 and at most 18 contiguous nucleotides of said sequence, or a sequence fully complementary thereto and of equal length,
    wherein (5') and (3') indicate respectively the 5' and 3' ends of said sequence and A is an adenyl residue, C is a cytidyl residue, T is a thymidyl residue and G is a guanidyl residue, and $R^1$ is a thymidine residue or a cytidyl residue,
    wherein said probe is able to hybridize with the 16S RNA of archaebacteria but which is incapable or very slightly capable of hybridizing with the 16S RNA of other procaryotes or the 18S RNA of eucaryotes or the 12S RNA of mitochondria.

9. A method of determining if bacteria are present in a sample comprising selectively detecting if a nucleotide sequence which codes for the 16S RNA in said bacteria is present by:
    (a) providing a sample which may contain said bacteria;
    (b) subjecting said sample to denaturation such that any of said nucleotide sequence which codes for said 16S RNA which is present in said sample is denatured into single-strands;
    (c) hybridizing any of said single-stranded nucleotide sequence with a labelled probe having the following nucleotide sequence or a sequence fully complementary to said probe end and of equal length;

(5') d-AAGGAGGTGATCCAG (3')

wherein (5') and (3') indicate respectively the 5' and 3' ends of said sequence and A is an adenyl residue, C is a cytidyl residue, T is a thymidyl residue and G is a guanidyl residue, under conditions which permit the formation of hybrids only when said labelled probe is completely complementary over its full length to said single-stranded nucleotide sequence; and (d) detecting if any of said hybridized labelled probe is present so as to determine if bacteria are present.

10. A method of determining if either eucaryotic or procaryotic organisms are present in a sample comprising detecting if a nucleotide sequence which is found in both eucaryotic or procaryotic organisms is present by:

(a) providing a sample which may contain said eucaryotic or procaryotic organisms;

(b) subjecting said sample to denaturation such that any of said nucleotide sequence which is present in said sample is denatured into single-strands;

(c) hybridizing any of said single-stranded sequence with a labelled probe having the following nucleotide sequence or a sequence fully complementary to said probe and of equal length;

(5') d-ACCTTGTTACGACTT (3'), wherein (3') and (5') indicate respectively the 3' and 5' ends of said sequence and A is an adenyl residue, C is a cytidyl residue, T is a thymidyl residue and C is a guanidyl residue, under conditions which permit the formation of hybrids only when said labelled probe is completely complementary over its full length to said single-stranded nucleotide sequence; and (d) detecting if any of said hybridized labelled probe is present so as to determine if either eucaryotic or procaryotic organisms are present.

11. A method for determining if archaebacteria are present in a sample comprising detecting if a nucleotide sequence which codes for the 16S RNA of said archaebacteria is present by:

(a) providing a sample which may contain said archaebacteria;

(b) subjecting said sample to denaturation such that any of said nucleotide sequence which codes for said 16S RNA which is present in said sample is denatured into single-strands;

(c) hybridizing any of said single-stranded nucleotide sequence with a labelled probe having the following nucleotide sequence or a sequence fully complementary to said probe and of equal length;

(5') GCGCCCCAR'CTCGTCGAA (3')

wherein (3') and (5') indicate respectively the 3' and 5' ends of said sequence and A is an adenyl residue, C is a cytidyl residue, T is a thymidyl residue and G is a guanidyl residue and R' is thymidyl residue or a cytidyl residue, under conditions which permit the formation of hybrids only when said labelled probe is completely complementary over its full length to said single-stranded nucleotide sequence; and (d) detecting if any of said hybridized labelled probe is present to determine if archaebacteria are present.

12. A method of selectively detecting if bacteria are present in a sample via detection of a nucleotide sequence which nucleotide sequence codes for a 16S RNA in said bacteria, said method comprising:

(a) providing a sample which may contain said bacteria;

(b) subjecting said sample to denaturation such that any of said nucleotide sequence which codes for said 16S RNA which is present in said sample is denatured into single-strands;

(c) hybridizing said single-stranded nucleotide sequence in bacteria with a labelled probe or a labelled probe having sequence fully complementary to said probe and of equal length, wherein the labeled probe is selected from the group consisting of the following group of sequences:

(5') d-AAAGGAGGT (3')
(5') d-AAGGAGGTGA (3')
(5') d-AAGGAGGTGAT (3')
(5') d-AAGGAGGTGATC (3')
(5') d-AAGGAGGTGATCC (3')
(5') d-AAGGAGGTGATCCA (3')

wherein (5') and (3') indicate respectively the 5' and 3' ends of said sequence and A is an adenyl residue, C is a cytidyl residue, T is a thymidyl residue and G is a guanidyl residue, under conditions which permit the formation of hybrids only when said labelled probe is completely complementary over its full length to said single-stranded nucleotide sequence; and (d) detecting if any of said hybridized labelled probe is present so as to determine if bacteria are present.

* * * * *

UNITED STATES PATENT AND TRADEMARK OFFICE
CERTIFICATE OF CORRECTION

PATENT NO. : 5,407,797
DATED : April 18, 1995
INVENTOR(S) : Philippe MARLIERE, et al.

It is certified that error appears in the above-indentified patent and that said Letters Patent is hereby corrected as shown below:

On the title page, Item [63] and Column 1, Lines 7-12, the Related U.S. Application Data should read:

--Continuation of Ser. No. 711,411, Jun. 5, 1991, abandoned, which is a continuation of Ser. No. 596,553, Oct. 12, 1990, abandoned, which is a continuation of Ser. No. 97,519, Sep. 28, 1987, abandoned; which was filed as International Application No. PCT/FR87/00108 on Apr. 3, 1987.--

Signed and Sealed this

Twelfth Day of September, 1995

Attest:

BRUCE LEHMAN

*Attesting Officer*      *Commissioner of Patents and Trademarks*